(12) United States Patent
Houser

(10) Patent No.: US 7,621,930 B2
(45) Date of Patent: Nov. 24, 2009

(54) ULTRASOUND MEDICAL INSTRUMENT HAVING A MEDICAL ULTRASONIC BLADE

(75) Inventor: Kevin L. Houser, Springboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 658 days.

(21) Appl. No.: 11/336,274

(22) Filed: Jan. 20, 2006

(65) Prior Publication Data

US 2007/0173871 A1 Jul. 26, 2007
US 2009/0131962 A2 May 21, 2009

(51) Int. Cl.
*A61B 17/32* (2006.01)
(52) U.S. Cl. ......................................... 606/169; 604/22
(58) Field of Classification Search .................... 606/27, 606/169, 159, 167; 604/21–22
See application file for complete search history.

(56) References Cited

U.S. PATENT DOCUMENTS

| | | |
|---|---|---|
| 4,452,473 A | 6/1984 | Ruschke |
| 4,696,667 A | 9/1987 | Masch |
| 4,979,952 A | 12/1990 | Kubota et al. |
| 5,057,119 A | 10/1991 | Clark et al. |
| 5,059,210 A | 10/1991 | Clark et al. |
| 5,156,613 A | 10/1992 | Sawyer |
| 5,167,725 A | 12/1992 | Clark et al. |
| 5,205,817 A * | 4/1993 | Idemoto et al. ............... 604/22 |
| 5,209,776 A | 5/1993 | Bass et al. |
| 5,242,385 A | 9/1993 | Strukel |
| 5,261,922 A | 11/1993 | Hood |
| 5,263,957 A | 11/1993 | Davison |
| 5,289,436 A | 2/1994 | Terhune |
| 5,306,280 A | 4/1994 | Bregen et al. |
| 5,318,570 A | 6/1994 | Hood et al. |
| 5,322,055 A | 6/1994 | Davison et al. |
| 5,324,297 A | 6/1994 | Hood et al. |

(Continued)

FOREIGN PATENT DOCUMENTS

EP 0695535 2/1996

(Continued)

OTHER PUBLICATIONS

LigaSure* Xtd, tyco Healthcare, Valleylab (Nov. 2002).

(Continued)

*Primary Examiner*—Michael Peffley
*Assistant Examiner*—Samantha Muro
(74) *Attorney, Agent, or Firm*—Verne E. Kreger, Jr.

(57) ABSTRACT

A first ultrasound medical instrument includes a medical ultrasonic blade having first, second and third blade portions. The second blade portion is more bendable than either of the first and third blade portions. A second ultrasound medical instrument includes a medical ultrasonic blade having a proximal blade portion and a distal blade portion. The distal blade portion bends more easily than does the proximal blade portion. The distal blade portion includes a distal end portion adapted to contact and ultrasonically treat patient tissue. A third ultrasonic medical instrument includes a medical ultrasonic blade. The medical ultrasonic blade includes a proximal blade portion having a centerline and includes a distal blade portion in contact with the proximal blade portion at a substantially planar interface. The interface is oriented at a non-zero angle with respect to a perpendicular to the centerline at the interface.

17 Claims, 5 Drawing Sheets

U.S. PATENT DOCUMENTS

| | | | |
|---|---|---|---|
| 5,324,299 A | 6/1994 | Davison et al. |
| 5,342,292 A | 8/1994 | Nita et al. |
| 5,372,585 A | 12/1994 | Tiefenbrun et al. |
| 5,383,883 A | 1/1995 | Wilk et al. |
| 5,647,851 A | 7/1997 | Pokras |
| 5,735,875 A | 4/1998 | Bonutti et al. |
| 5,807,310 A | 9/1998 | Hood |
| 5,810,869 A | 9/1998 | Kaplan et al. |
| 5,836,897 A | 11/1998 | Sakurai et al. |
| 5,843,109 A | 12/1998 | Mehta et al. |
| 5,853,290 A | 12/1998 | Winston |
| 5,893,880 A | 4/1999 | Egan et al. |
| 5,895,412 A | 4/1999 | Tucker |
| 5,910,150 A | 6/1999 | Saadat |
| 5,935,143 A | 8/1999 | Hood |
| 5,941,887 A | 8/1999 | Steen et al. |
| 5,957,943 A | 9/1999 | Vaitekunas |
| 5,989,275 A * | 11/1999 | Estabrook et al. ........... 606/169 |
| 6,004,335 A | 12/1999 | Vaitekunas et al. |
| 6,033,375 A | 3/2000 | Brumbach |
| 6,051,010 A | 4/2000 | DiMatteo et al. |
| 6,053,906 A | 4/2000 | Honda et al. |
| 6,063,098 A * | 5/2000 | Houser et al. ............... 606/169 |
| 6,206,877 B1 | 3/2001 | Kese et al. |
| 6,217,591 B1 | 4/2001 | Egan et al. |
| 6,270,471 B1 | 8/2001 | Hechel et al. |
| 6,283,981 B1 | 9/2001 | Beaupre |
| 6,325,811 B1 | 12/2001 | Messerly |
| 6,352,532 B1 | 3/2002 | Kramer et al. |
| 6,409,743 B1 | 6/2002 | Fenton, Jr. |
| 6,436,114 B1 | 8/2002 | Novak et al. |
| 6,458,142 B1 | 10/2002 | Faller et al. |
| 6,491,708 B2 | 12/2002 | Madan et al. |
| 6,526,976 B1 | 3/2003 | Baran |
| 6,561,983 B2 | 5/2003 | Cronin et al. |
| 6,562,059 B2 | 5/2003 | Edwards et al. |
| 6,616,450 B2 | 9/2003 | Mossle et al. |
| 6,623,444 B2 | 9/2003 | Babaev |
| 6,689,086 B1 | 2/2004 | Nita et al. |
| 6,695,782 B2 | 2/2004 | Ranucci et al. |
| 6,699,214 B2 | 3/2004 | Gellman |
| 6,702,761 B1 | 3/2004 | Damadian et al. |
| 6,887,221 B1 | 5/2005 | Baillargeon et al. |
| 6,887,252 B1 | 5/2005 | Okada et al. |
| 6,908,466 B1 | 6/2005 | Bonutti et al. |
| 7,018,354 B2 | 3/2006 | Tazi |
| 7,335,997 B2 | 2/2008 | Wiener |
| 7,338,463 B2 | 3/2008 | Vigil |
| 2001/0025184 A1 | 9/2001 | Messerly |
| 2002/0045860 A1 | 4/2002 | Sussman et al. |
| 2002/0103438 A1 | 8/2002 | Cronin et al. |
| 2002/0138037 A1 | 9/2002 | Weimann |
| 2002/0193798 A1 | 12/2002 | Oh et al. |
| 2004/0006347 A1 | 1/2004 | Sproul |
| 2004/0039242 A1 | 2/2004 | Tolkoff et al. |
| 2004/0176686 A1 * | 9/2004 | Hare et al. .................. 600/431 |
| 2005/0004589 A1 | 1/2005 | Okada et al. |
| 2005/0038340 A1 | 2/2005 | Vaezy et al. |
| 2005/0049546 A1 | 3/2005 | Messerly et al. |
| 2005/0085728 A1 | 4/2005 | Fukuda |
| 2005/0131401 A1 * | 6/2005 | Malecki et al. ............... 606/27 |
| 2005/0143726 A1 | 6/2005 | Bortkiewicz |
| 2006/0257819 A1 | 11/2006 | Johnson |
| 2007/0060926 A1 | 3/2007 | Escaf |
| 2007/0239028 A1 | 10/2007 | Houser et al. |

FOREIGN PATENT DOCUMENTS

| | | | |
|---|---|---|---|
| EP | 1108394 | | 6/2001 |
| EP | 1543854 | | 6/2005 |
| EP | 1707131 | | 10/2006 |
| WO | 02/076685 | | 10/2002 |
| WO | 03/002189 | | 1/2003 |
| WO | WO 03/024513 | | 3/2003 |
| WO | WO 2004/060447 | | 7/2004 |
| WO | WO 2005/056104 | * | 6/2005 |
| WO | 2005/084251 | | 9/2005 |

OTHER PUBLICATIONS

International Search Report issued regarding International Application No. PCT/US07/01705 (Nov. 1, 2007).

* cited by examiner

ULTRASOUND MEDICAL INSTRUMENT HAVING A MEDICAL ULTRASONIC BLADE

FIELD OF THE INVENTION

The present invention is related generally to ultrasound medical instruments, and more particularly to an ultrasound medical instrument having a medical ultrasonic blade.

BACKGROUND OF THE INVENTION

Known ultrasound medical instruments include ultrasonic surgical blades. Ultrasonic surgical instruments are also known which include ultrasonic surgical shears having an ultrasonic surgical blade (in the form of a titanium rod), a clamping arm operable to open and close toward the blade, a tissue pad attached to the clamping arm, and a device for exerting a clamping force on the clamping arm which creates a clamping pressure on a blood vessel which is positioned between the tissue pad and the blade. The result of the ultrasonically-vibrating ultrasonic surgical blade and the clamping pressure on the blood vessel is a coaptation of the blood vessel (a bringing together of the walls of the blood vessel), a transection (a cutting) of the coaptated blood vessel, and a coagulation (a sealing) of the coaptated cut ends of the blood vessel. Articulating surgical staplers, scissors, and graspers are also known.

Still, scientists and engineers continue to seek improved ultrasound medical instruments having a medical ultrasonic blade.

SUMMARY OF THE INVENTION

A first embodiment of the invention is for an ultrasound medical instrument including a medical ultrasonic blade. The medical ultrasonic blade has a length and includes first, second and third blade portions. The second blade portion is located lengthwise between the first and third blade portions, the first blade portion is located proximal the second blade portion, and the third blade portion is located distal the second blade portion. The first and third blade portions each have a larger transverse area and the second blade portion has a smaller transverse area. The second blade portion is more bendable than either of the first and third blade portions.

A second embodiment of the invention is for an ultrasound medical instrument including a medical ultrasonic blade. The medical ultrasonic blade has a length and includes a proximal blade portion and a distal blade portion. The proximal blade portion has a larger transverse area and the distal blade portion has a smaller transverse area. The distal blade portion bends more easily than does the proximal blade portion. The distal blade portion includes a distal end portion adapted to contact and ultrasonically treat patient tissue.

A third embodiment of the invention is for an ultrasound medical instrument including a medical ultrasonic blade. The medical ultrasonic blade includes a proximal blade portion having a centerline and includes a distal blade portion in contact with the proximal blade portion at a substantially planar interface. The interface is oriented at a non-zero angle with respect to a perpendicular to the centerline at the interface.

Several benefits and advantages are obtained from one or more of the embodiments of the invention. In one example of the first embodiment, the first and second blade portions are rigid, and the second blade portion is controllably bent during a medical procedure to more easily access a target site in a patient. In one example of the second embodiment, the proximal blade portion is rigid, and the distal blade portion is controllably bent during a medical procedure for the distal end portion of the distal blade portion to more easily access a target site in a patient to contact and ultrasonically treat patient tissue. In one example of the third embodiment, relative rotation, about the interface, of the proximal and distal blade portions articulates the distal blade portion with respect to the proximal blade portion.

The present invention has, without limitation, application with straight or curved ultrasonic surgical blades, with or without clamping arms, and further in hand-activated instruments as well as in robotic-assisted instruments.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described embodiments, examples, etc. can be combined with any one or more of the other following-described embodiments, examples, etc.

Figure 1:
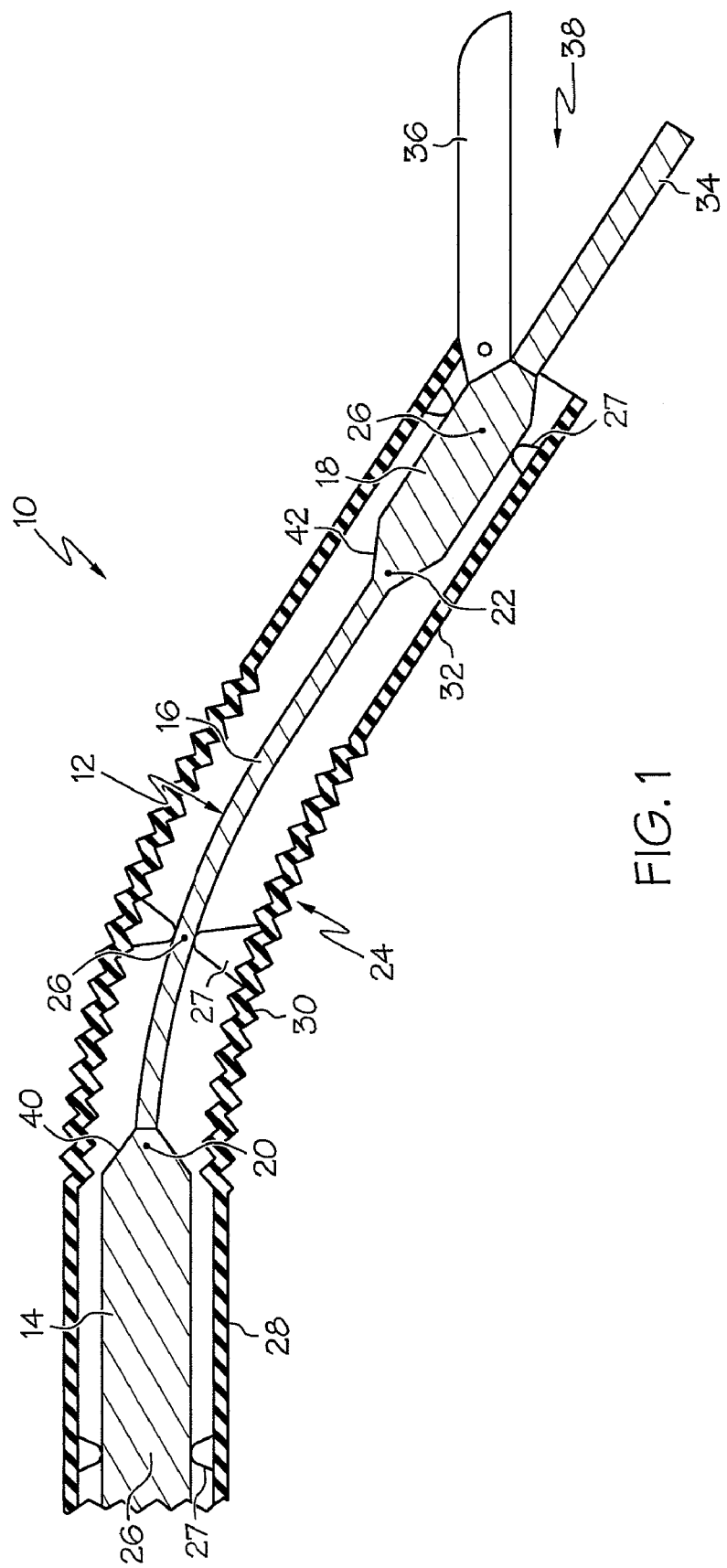
FIG. 1 is a schematic cross-sectional view of a portion (with the handpiece and the sheath-articulation control knobs, etc. omitted for clarity) of a first embodiment of an ultrasound medical instrument of the invention wherein the second blade portion is substantially ½ of a resonant-longitudinal-wavelength long.

Referring now to the Figures, in which like numerals indicate like elements, FIG. 1 illustrates a first embodiment of the invention. A first expression of the embodiment of FIG. 1 is for an ultrasound medical instrument 10 including a medical ultrasonic blade 12. The medical ultrasonic blade 12 has a length and includes first, second and third blade portions 14, 16 and 18. The second blade portion 16 is located lengthwise between the first and third blade portions 14 and 18, the first blade portion 14 is located proximal the second blade portion 16, and the third blade portion 18 is located distal the second blade portion 16. The first and third blade portions 14 and 18 each have a larger transverse area and the second blade portion 16 has a smaller transverse area. The second blade portion 16 is more bendable than either of the first and third blade portions 14 and 18. It is further noted that ultrasonic vibration can be any one, or any combination, of longitudinal, transverse, and torsional vibration.

In one enablement of the embodiment of FIG. 1, the medical ultrasonic blade 12 is a monolithic blade. In one variation, the medical ultrasonic blade 12 includes first and second longitudinal vibration antinodes 20 and 22, wherein the first blade portion 14 transitions to the second blade portion 16 proximate the first longitudinal vibration antinode 20, and wherein the second blade portion 16 transitions to the third blade portion 18 proximate the second longitudinal vibration antinode 22.

In one application of the embodiment of FIG. 1, the ultrasound medical instrument 10 also includes a user-actuated articulated sheath 24 which surrounds the medical ultrasonic blade 12. In one variation, the medical ultrasonic blade 12 includes three (meaning at least three) longitudinal vibration nodes 26 located, one each, on the first, second and third blade portions 14, 16 and 18. It is noted that one or more additional longitudinal vibration nodes may, or may not, be present between any one or two of the three longitudinal vibration nodes 26. In one modification, the sheath 24 contacts (i.e., directly contacts or indirectly contacts through at least one intervening member 27 such as a silicone intervening member) the first, second and third blade portions 14, 16 and 18 at a corresponding one of the three longitudinal vibration nodes 26. In one example, the sheath 24 includes a rigid first sheath portion 28 contacting the first blade portion 14 at the first longitudinal vibration node (the leftmost node 26 of FIG. 1), a flexible second sheath portion 30 contacting the second blade portion 16 at the second longitudinal vibration node (the middle node 26 of FIG. 1), and a rigid third sheath portion 32 contacting the third blade portion 18 at the third longitudinal vibration node (the rightmost node 26 of FIG. 1). In one deployment, the sheath 24 has only two articulation positions (i.e., straight and fully articulated). In a different deployment, the sheath 24 has a number of intermediate bent positions between a straight position and a fully articulated position depending on the number of energy efficient curves the blade 12 can be formed to. In one arrangement, such energy efficient curves minimize vibrational energy going into non-longitudinal vibrational modes.

Figure 2:
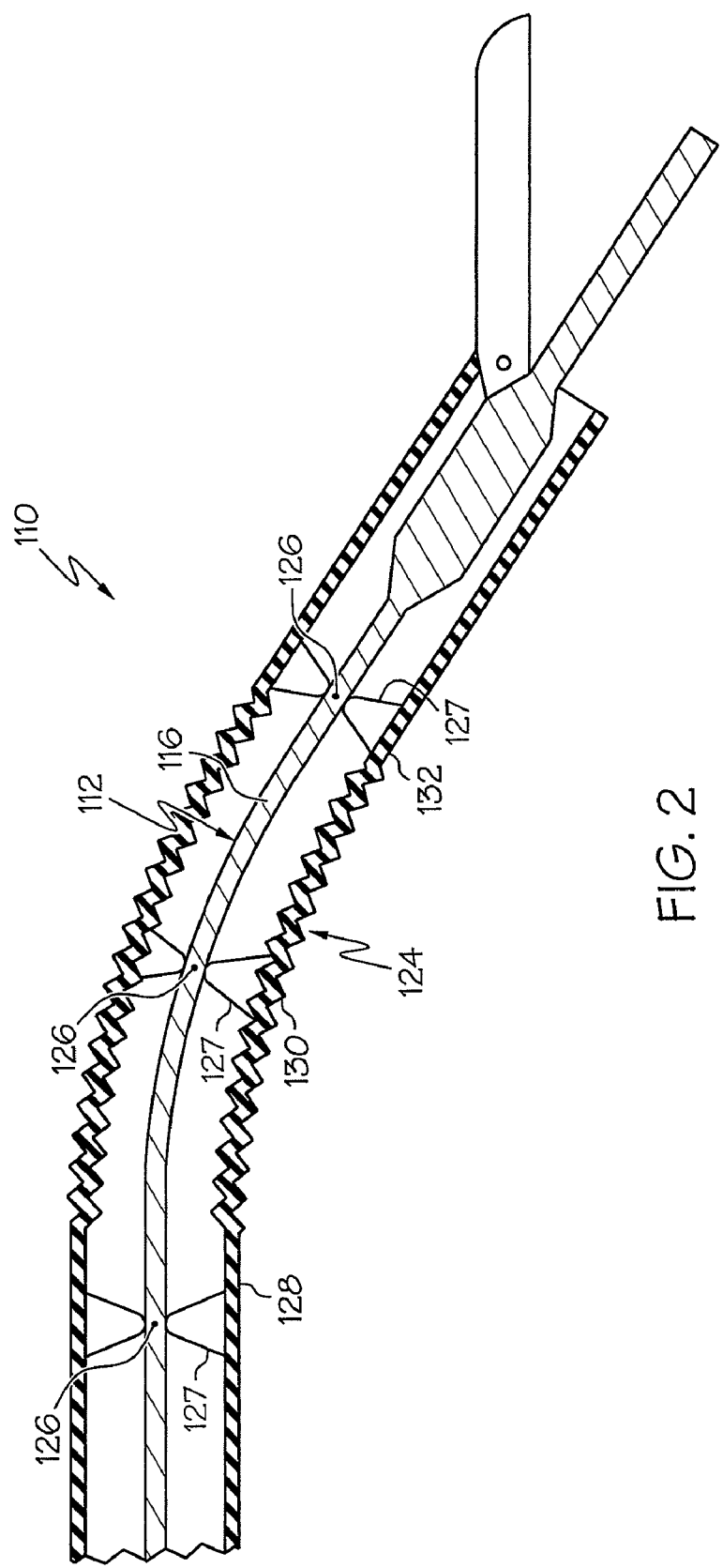
FIG. 2 is view, as in FIG. 1, but of an alternate embodiment of the ultrasound medical instrument wherein the second blade portion spans multiple ½ resonant longitudinal wavelengths.

In the same or a different variation, as illustrated in the alternate embodiment of the ultrasound medical instrument 110 of FIG. 2, the medical ultrasonic blade 112 includes at least two longitudinal vibration nodes 126 located on the second blade portion 116. In one variation, the sheath 124 contacts (i.e., directly contacts or indirectly contacts through at least one intervening member 127 such as a silicone intervening member) the second blade portion 116 at the at-least-two longitudinal vibration nodes 126. In one modification, the sheath 124 includes two rigid sheath portions 128 and 132 and one flexible sheath portion 130, wherein the flexible sheath portion 130 contacts the second blade portion 116 at least one of the two longitudinal vibration nodes 126, and wherein the flexible sheath portion 130 is disposed between the two rigid sheath portions 128 and 132. In one example, the two rigid sheath portions 128 and 132 each contact the second blade portion 116 at a corresponding one of the at-least-two longitudinal vibration nodes 126.

In one enablement of the application which includes the sheath 24 of the embodiment of FIG. 1, the medical ultrasonic blade 12 includes a fourth blade portion 34 adapted to contact and ultrasonically treat patient tissue, wherein the fourth blade portion 34 is disposed distal of the third blade portion 18. In one variation, the ultrasound medical instrument 10 also includes a user-actuated clamp arm 36 pivotally attached to the sheath 24 proximate the fourth blade portion 34, wherein the clamp arm 36 and the medical ultrasonic blade 12 at least in part define an ultrasonic surgical shears 38. The tissue pad and clamping arm control mechanism have been omitted from FIG. 1 for clarity.

In one employment of the embodiment of FIG. 1, the first and third blade portions 14 and 18 are essentially rigid. In the same or a different employment, the medical ultrasonic blade 12 includes first and second neck portions 40 and 42 joining, respectively, the first and second blade portions 14 and 16 and the second and third blade portions 16 and 18. In one modification, the medical ultrasonic blade 12 is substantially cylindrical from the first blade portion 14 to the third blade portion 18, wherein the first, second and third blade portions 14, 16 and 18 each have a substantially constant diameter, and wherein the diameter of the second blade portion 16 is smaller than the diameter of either of the first and third blade portions 14 and 18. In one illustration, the diameter of the second blade portion 16 is between substantially one and two millimeters, and the diameter of the first and third blade portions is between substantially three and five millimeters. In one choice of materials, the medical ultrasonic blade 12 consists essentially of a titanium alloy. In one modification, the medical ultrasonic blade 12 includes first and second longitudinal vibration antinodes 20 and 22, and the first neck portion 40 is disposed proximate the first longitudinal vibration antinode 20 and the second neck portion 42 is disposed proximate the second longitudinal vibration antinode 22.

Figure 3:
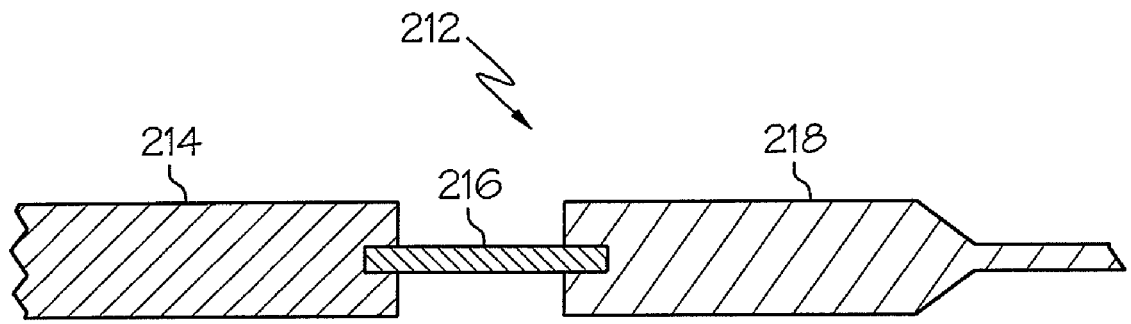
FIG. 3 is a view, as in FIG. 1, but of only an alternate embodiment of the medical ultrasonic blade, wherein the second blade portion is joined to the first blade portion by a dowel press fit.

In one construction, as illustrated in the alternate embodiment of the medical ultrasonic blade 212 of FIG. 3, wherein the medical ultrasonic blade 212 is not a monolithic blade, the second blade portion 216 is joined to the first blade portion 214 by a dowel press fit and is joined to the third blade portion 218 by a dowel press fit. In one illustration, the second blade portion 216 consists essentially of titanium or nitinol. In the same or a different illustration, the length of the second blade portion is less than ½ wave (a wave being the length of a resonant-longitudinal-wavelength of the medical ultrasonic blade which depends essentially on the material of the blade and the frequency at which it is run) and in one example is less than ⅛ wave. In a different construction, as illustrated in the alternate embodiment of the medical ultrasonic blade 312 of FIG. 4, wherein the medical ultrasonic blade 312 is not a monolithic blade, the second blade portion 316 is joined to the first blade portion 314 by a ball-and-socket type attachment and is joined to the third blade portion 318 by a dowel press fit. Other attachments between blade portions are left to those skilled in the art.

Figure 5:
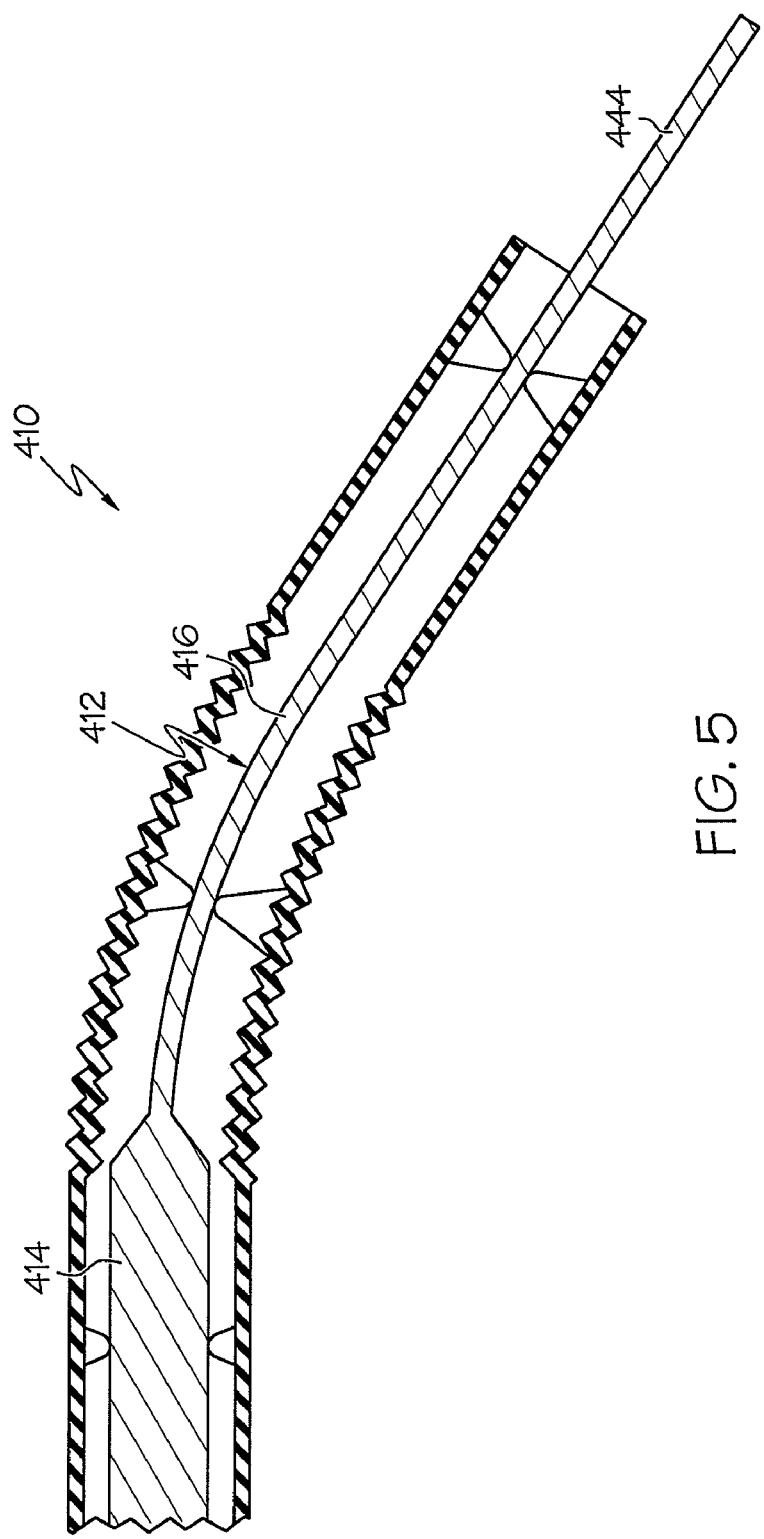
FIG. 5 is a schematic cross-sectional view of a portion of a second embodiment of an ultrasound medical instrument of the invention which lacks the third blade portion of the embodiment of FIG. 1.

Referring again to the Figures, FIG. 5 illustrates a second embodiment of the invention. A first expression of the embodiment of FIG. 5 is for an ultrasound medical instrument 410 including a medical ultrasonic blade 412. The medical ultrasonic blade 412 has a length and includes a proximal blade portion 414 and a distal blade portion 416. The proximal blade portion 414 has a larger transverse area and the distal blade portion 416 has a smaller transverse area. The distal blade portion 416 bends more easily than does the proximal blade portion 414. The distal blade portion 416 includes a distal end portion 444 adapted to contact and ultrasonically treat patient tissue.

In one example of the first expression of the embodiment of FIG. 5, the additional ½ wave needed to neck up and create the larger diameter end effector of the embodiment of FIG. 1 is eliminated making it possible to place the articulation joint closer to the distal end of the ultrasound medical instrument.

Figure 4:
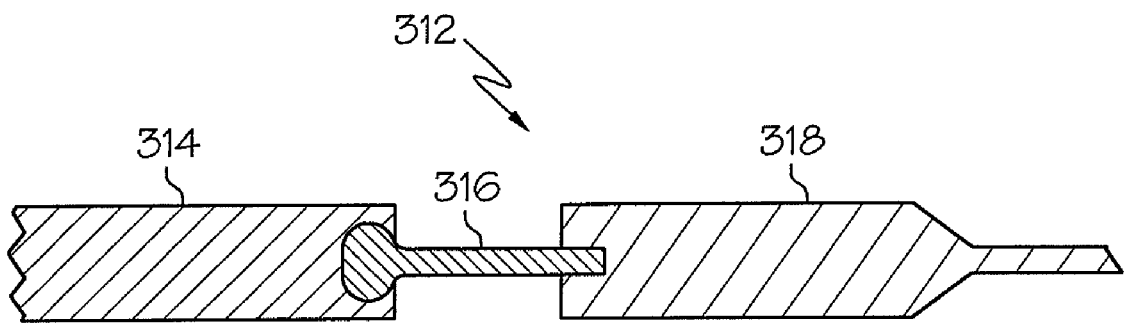
FIG. 4 is a view, as in FIG. 3, but of an alternate embodiment of the medical ultrasonic blade, wherein the second blade portion is joined to the first blade portion by a ball-and-socket type attachment.

The enablements, applications, etc. of the embodiment of FIG. 1 and of the alternate embodiments of FIGS. 2-4 are equally applicable (without the presence of the third blade portion) to the embodiment of FIG. 5.

Figure 6:
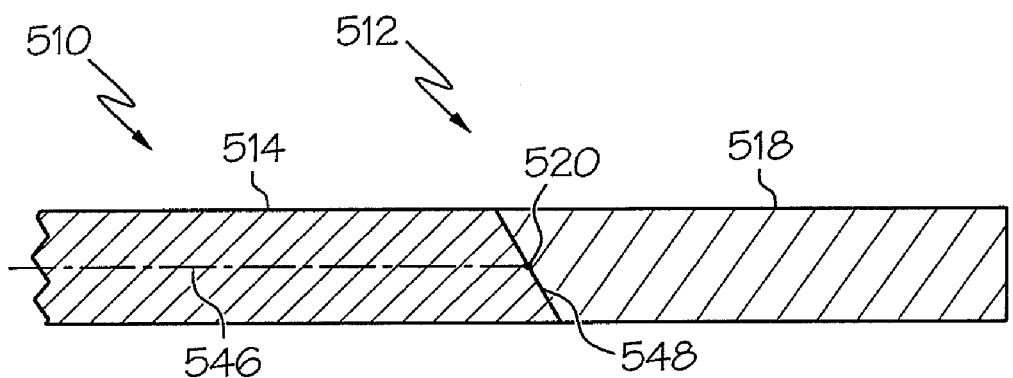
FIG. 6 is a schematic cross-sectional view of a portion of a third embodiment of an ultrasound medical instrument of the invention having a medical ultrasonic blade which includes two blade portions having a tilted interface, wherein relative rotation of the blade portions causes articulation of the distal blade portion with respect to the proximal blade portion.

Referring again to the Figures, FIG. 6 illustrates a third embodiment of the invention. A first expression of the embodiment of FIG. 6 is for an ultrasound medical instrument 510 including a medical ultrasonic blade 512. The medical ultrasonic blade 510 includes a proximal blade portion 514 having a centerline 546 and includes a distal blade portion 518 in contact with the proximal blade portion 514 at a substantially planar interface 548. The interface is oriented at a non-zero angle with respect to a perpendicular to the centerline 546 at the interface 548.

In one arrangement of the embodiment of FIG. 6, the non-zero angle has a range from substantially thirty degrees to substantially sixty degrees. In one variation, the non-zero angle is substantially forty-five degrees.

Figure 7:
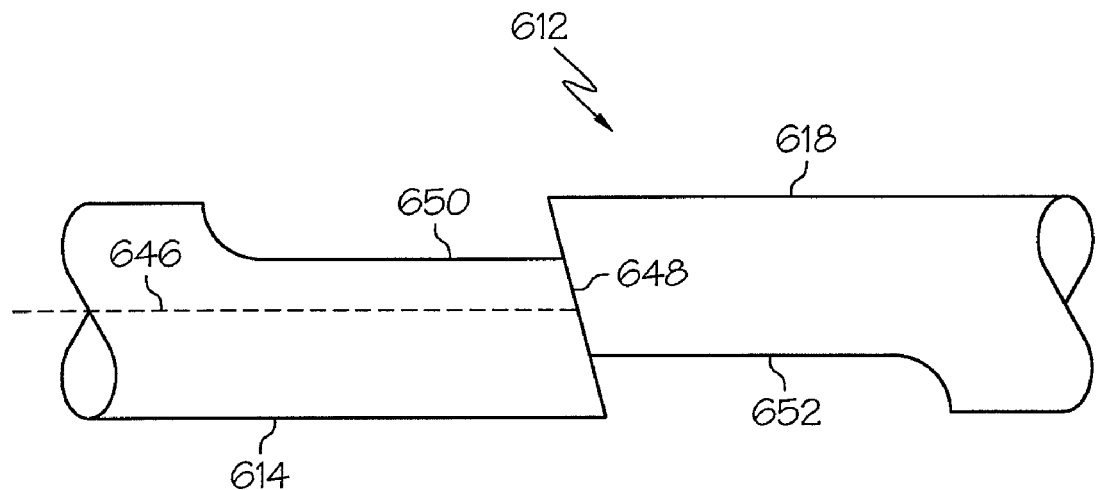
FIGS. 7 and 8 are side-elevational views, before-and-after-rotation, of an alternate embodiment of the medical ultrasonic blade wherein the blade portions have areas of removed material.
Figure 8:
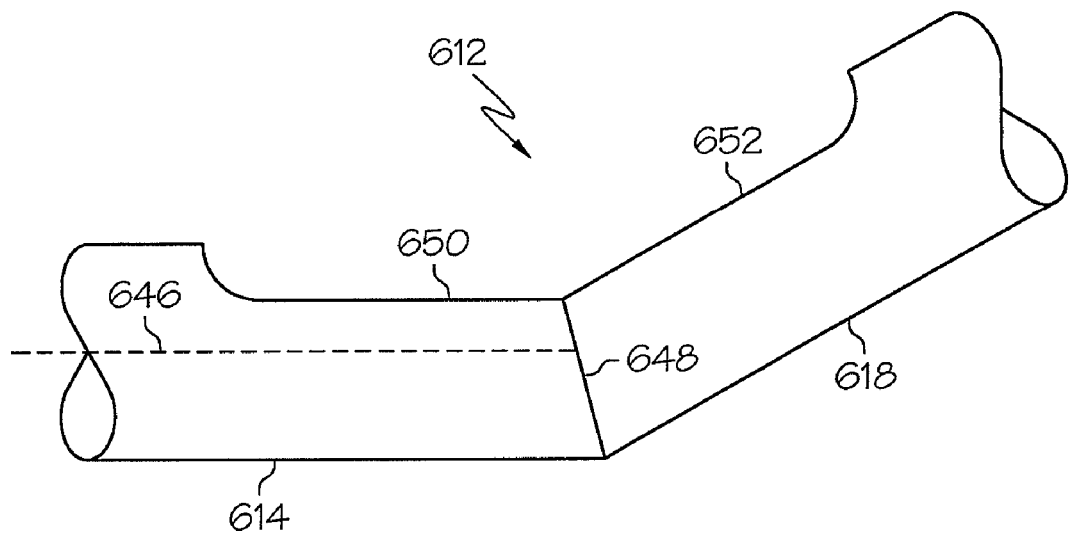

In one enablement of the embodiment of FIG. 6, the proximal and distal blade portions 514 and 518 each have a shape of a substantially solid circular cylinder. In a different enablement, as shown in the alternate embodiment of FIGS. 7 and 8, the proximal and distal blade portions 614 and 618 each have a shape of a substantially solid circular cylinder having at least one area 650 and 652 of removed (surface and/or non-surface) material, wherein the medical ultrasonic blade 612 has an unarticulated position (see FIG. 7) and a fully articulated position (see FIG. 8), and wherein the at-least-one areas 650 and 652 of the proximal and distal blade portions 614 and 618 are substantially rotationally opposed about the centerline 646 in the unarticulated position and are substantially rotationally aligned about the centerline 646 in the fully articulated position. In one example, relative 180-degree rotation, about the interface 648, of the proximal and distal blade portions 614 and 618 articulates the distal blade portion 618 with respect to the proximal blade portion 614 portion from the unarticulated position to the fully articulated position. In one application, in the unarticulated position the substantially rotationally opposed areas 650 and 652 balance the medical ultrasonic blade 612, and in the fully articulated position the substantially aligned areas balance the blade asymmetry, as can be understood by those skilled in the art.

It is within the ordinary level of skill of the artisan to employ mechanisms (such as those employed in conventional flexible endoscopes, articulating surgical staplers, articulating surgical scissors and/or articulating surgical graspers, and the like) to bend or rotate the appropriate blade portion or portions of the above-described embodiments of ultrasound medical instruments to articulate the medical ultrasonic blade, when manual bending or rotation during a medical procedure is not desired.

Several benefits and advantages are obtained from one or more of the embodiments of the invention. In one example of the first embodiment, the first and second blade portions are rigid, and the second blade portion is controllably bent during a medical procedure to more easily access a target site in a patient. In one example of the second embodiment, the proximal blade portion is rigid, and the distal blade portion is controllably bent during a medical procedure for the distal end portion of the distal blade portion to more easily access a target site in a patient to contact and ultrasonically treat patient tissue. In one example of the third embodiment, relative rotation, about the interface, of the proximal and distal blade portions articulates the distal blade portion with respect to the proximal blade portion.

While the present invention has been illustrated by a description of several embodiments, it is not the intention of the applicants to restrict or limit the spirit and scope of the appended claims to such detail. Numerous other variations, changes, and substitutions will occur to those skilled in the art without departing from the scope of the invention. For instance, the ultrasound medical instruments have application in robotic assisted surgery taking into account the obvious modifications of such systems, components and methods to be compatible with such a robotic system. It will be understood that the foregoing description is provided by way of example, and that other modifications may occur to those skilled in the art without departing from the scope and spirit of the appended Claims.

What is claimed is:

1. An ultrasound medical instrument comprising:
    a medical ultrasonic blade having a length and including first, second and third blade portions, wherein the second blade portion is disposed lengthwise between the first and third blade portions and includes at least two longitudinal vibration nodes thereon, wherein the first blade portion is disposed proximal the second blade portion, wherein the third blade portion is disposed distal the second blade portion, wherein the first blade portion has a first transverse area, the second blade portion has a second transverse area and the third blade portion has a third transverse area, the first and third transverse areas each being greater than the second transverse area, and wherein the second blade portion is more bendable than either of the first and third blade portions; and
    a user-actuated articulated sheath received over the medical ultrasonic blade.

2. The ultrasound medical instrument of claim 1, wherein the medical ultrasonic blade is a monolithic blade.

3. The ultrasound medical instrument of claim 2, wherein the medical ultrasonic blade includes first and second longitudinal vibration antinodes, wherein the first blade portion transitions to the second blade portion proximate the first longitudinal vibration antinode, and wherein the second blade portion transitions to the third blade portion proximate the second longitudinal vibration antinode.

4. The ultrasound medical instrument of claim 1, wherein the medical ultrasonic blade further includes two longitudinal vibration nodes located, one each, on the first and third blade portions.

5. The ultrasound medical instrument of claim 4, wherein the sheath contacts the first, second and third blade portions at the longitudinal vibration nodes.

6. The ultrasound medical instrument of claim 5, wherein the sheath includes a rigid first sheath portion contacting the longitudinal vibration node of the first blade portion, a flexible second sheath portion contacting at least one of the longitudinal vibration nodes of the second blade portion, and a rigid third sheath portion contacting the longitudinal vibration node of the third blade portion.

7. The ultrasound medical instrument of claim 6, wherein the sheath contacts each of the longitudinal vibration nodes of the second blade portion.

8. The ultrasound medical instrument of claim 7, wherein the two rigid sheath portions each contact the second blade portion at a corresponding one of the at-least-two longitudinal vibration nodes.

9. The ultrasound medical instrument of claim 1, wherein the medical ultrasonic blade includes a fourth blade portion adapted to contact and ultrasonically treat patient tissue, wherein the fourth blade portion is disposed distal of the third blade portion.

10. The ultrasound medical instrument of claim 9, also including a user-actuated clamp arm pivotally attached to the sheath proximate the fourth blade portion, wherein the clamp arm and the medical ultrasonic blade at least in part define an ultrasonic surgical shears.

11. The ultrasound medical instrument of claim 1, wherein the medical ultrasonic blade includes first and second neck portions joining, respectively, the first and second blade portions and the second and third blade portions, wherein the medical ultrasonic blade is substantially cylindrical from the first blade portion to the third blade portion, wherein the first, second and third blade portions each have a substantially constant diameter, and wherein the diameter of the second blade portion is smaller than the diameter of either of the first and third blade portions.

12. The ultrasound medical instrument of claim 11, wherein the medical ultrasonic blade includes first and second longitudinal vibration antinodes, and wherein the first neck portion is disposed proximate the first longitudinal vibration antinode and the second neck portion is disposed proximate the second longitudinal vibration antinode.

13. The ultrasonic medical instrument of claim 1, wherein the second blade portion is joined to the first blade portion by a dowel press fit and is joined to the third blade portion by a dowel press fit.

14. The ultrasonic medical instrument of claim 1, wherein the second blade portion is joined to the first blade portion by a ball-and-socket type attachment.

15. The ultrasonic medical instrument of claim 1, wherein the first and third blade portions are essentially rigid.

16. An ultrasound medical instrument comprising:
a medical ultrasonic blade having a length and including first, second and third blade portions, each of the first, second and third blade portions including at least one longitudinal vibration node, wherein the second blade portion is disposed lengthwise between the first and third blade portions, wherein the first blade portion is disposed proximal the second blade portion, wherein the third blade portion is disposed distal the second blade portion, wherein the first blade portion has a first transverse area, the second blade portion has a second transverse area and the third blade portion has a third transverse area, the first and third transverse areas each being greater than the second transverse area, and wherein the second blade portion is more bendable than either of the first and third blade portions; and
a user-actuated articulated sheath received over the medical ultrasonic blade, the sheath including a rigid first sheath portion contacting the longitudinal vibration node of the first blade portion, a flexible second sheath portion contacting the longitudinal vibration node of the second portion, and a rigid third sheath portion contacting the longitudinal vibration node of the third portion.

17. The ultrasonic medical instrument of claim 16 wherein the second portion of the medical ultrasonic blade includes at least two longitudinal vibration node.

\* \* \* \* \*

UNITED STATES PATENT AND TRADEMARK OFFICE
CERTIFICATE OF CORRECTION

| | | |
|---|---|---|
| PATENT NO. | : 7,621,930 B2 | Page 1 of 1 |
| APPLICATION NO. | : 11/336274 | |
| DATED | : November 24, 2009 | |
| INVENTOR(S) | : Houser | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 963 days.

Signed and Sealed this

Second Day of November, 2010

David J. Kappos
*Director of the United States Patent and Trademark Office*